(12) United States Patent
Lavrentovich et al.

(10) Patent No.: US 10,350,597 B2
(45) Date of Patent: Jul. 16, 2019

(54) LIQUID CRYSTALS WITH PATTERNED MOLECULAR ORIENTATION AS AN ELECTROLYTIC ACTIVE MEDIUM

(71) Applicant: Kent State University, Kent, OH (US)

(72) Inventors: Oleg D. Lavrentovich, Kent, OH (US); Qi-Huo Wei, Hudson, OH (US); Sergij V. Shiyanovskii, Stow, OH (US); Chenhui Peng, Kent, OH (US); Yubing Guo, Kent, OH (US)

(73) Assignee: Kent State University, Kent, OH (US)

( * ) Notice: Subject to any disclaimer, the term of this patent is extended or adjusted under 35 U.S.C. 154(b) by 147 days.

(21) Appl. No.: 15/358,532

(22) Filed: Nov. 22, 2016

(65) Prior Publication Data
US 2017/0144148 A1 May 25, 2017

Related U.S. Application Data

(60) Provisional application No. 62/259,190, filed on Nov. 24, 2015, provisional application No. 62/403,918, filed on Oct. 4, 2016.

(51) Int. Cl.
*G01N 27/447* (2006.01)
*G01N 27/453* (2006.01)
(Continued)

(52) U.S. Cl.
CPC ...... *B01L 3/50273* (2013.01); *B01F 13/0076* (2013.01); *B01L 3/502784* (2013.01);
(Continued)

(58) Field of Classification Search
CPC .......... G01N 27/447; G01N 27/44704; G01N 27/44721; G01N 27/44726; G01N 27/453
See application file for complete search history.

(56) References Cited

U.S. PATENT DOCUMENTS 6,897,915 B1 * 5/2005 Lavrentovich .... G02F 1/133377
349/115
9,146,415 B2 * 9/2015 Baek ................. B01J 13/14
(Continued)

OTHER PUBLICATIONS

Lazo et al., "Liquid crystal-enabled electrophoresis of spheres in a nematic medium with negative dielectric anisotropy," Phil. Trans, R. Soc. A 371, 20120255 (2013) (Year: 2013).*
(Continued)

*Primary Examiner* — Alexander S Noguerola
(74) *Attorney, Agent, or Firm* — Fay Sharpe LLP

(57) ABSTRACT

A transport device comprises: a fluid cell comprising parallel substrates; an anisotropic electrolyte disposed in the fluid cell; and electrodes configured to apply an AC electric field to the anisotropic electrolyte disposed in the fluid cell. A substrate of the fluid cell includes a pattern that induces a director distortion pattern in the anisotropic electrolyte disposed in the fluid cell. The director distortion pattern has a gradient configured to induce electrokinetic flow of the anisotropic electrolyte in the fluid cell in response to the AC electric field applied by the electrodes. Cargo, such as particles, gas bubbles, or fluid, is dispersed in the anisotropic electrolyte and transported in the fluid cell by the induced electrokinetic flow of the anisotropic electrolyte. The induced electrokinetic flow may be linear, curvilinear, circular so as to induce mixing, depending on the predesigned director pattern. The director pattern might be nonsingular (defect free) or may contain defects such as disclinations that produce pumping effects and can trap cargo at a core of the disclination.

21 Claims, 11 Drawing Sheets

(51) Int. Cl.
  *B01L 3/00* (2006.01)
  *B01F 13/00* (2006.01)
(52) U.S. Cl.
  CPC ..... *G01N 27/44747* (2013.01); *B01L 2300/0645* (2013.01); *B01L 2300/0867* (2013.01); *B01L 2300/168* (2013.01); *B01L 2400/0418* (2013.01); *B01L 2400/0421* (2013.01); *G01N 27/44704* (2013.01)

(56) References Cited

U.S. PATENT DOCUMENTS

| | | | | |
|---|---|---|---|---|
| 2015/0261023 | A1* | 9/2015 | Lavrentovich | G02F 1/1313 349/1 |
| 2017/0144148 | A1* | 5/2017 | Lavrentovich | B01L 3/50273 |

OTHER PUBLICATIONS

Lazo et al., "Liquid crystal-enabled electro-osmosis through spatial charge separation in distorted regions as a novel mechanism of electrokinetics," Nat. Commun. 5-5033 (2014) (Year: 2014).*
Sung-Jo Kim et al., Asymmetric motion of bubble in nematic liquid crystal induced by symmetry-broken evaporation, 2016 EPL 115 16002 (Year: 2016).*
Hernàndez-Navarro et al., AC electrophoresis of microdroplets in anisotropic liquids: transport, assembling and reaction, Soft Matter, 2013, 9, 7999 (Year: 2013).*
Hoogboom et al., "LCD alignment layers. Controlling nematic domain properties," J. Mater. Chem., 2006, 16, 1305-1314 (Year: 2006).*
C.-Y. Lee, C.-L. Chang, Y.-N. Wang, L.-M. Fu, Microfluidic Mixing; A Review, International Journal of Molecular Sciences, 12 (2011) 3263-3287.
T.M. Squires, M.Z. Bazant, Breaking symmetries in induced charge electro-osmosis and electrophoresis, Journal of Fluid Mechanics, 560 (2006) 65-102.
Q. Guo, A.K. Srivastava, V.G. Chigrinov, H.S. Kwok, Polymer and azo-dye composite: a photo-alignment layer for liquid crystals, Liquid Crystals, 41 (2014) 1465-1472.
I. Lazo, O.D. Lavrentovich, Liquid-crystal-enabled electrophoresis of spheres in a nematic medium with negative dielectric anisotropy, Philosophical Transactions of the Royal Society A: Mathematical, Physical and Engineering Sciences, 371 (2013) 20120255.
S. Hernàndez-Nevarro, P. Tierno, J.A. Farrera, J. Ignés-Mullol, F. Sagués, Reconfigurable Swarms of Colloidal Particles Electrophoretically Drivein Nematic Liquid Crystals, 25$^{th}$ International Liquid Crystal Conference (ILCC 2014), published online Jul. 6, 2015.
J.A. Levitan, S. Devasenathipathy, V. Studer, Y. Ben, T. Thorsen, T.M. Squires, M.Z. Bazant, Experimental observation of induced-charge electro-osmosis around a metal wire in a microchannel, Colloids and Surfaces A: Physicochemical and Engineering Aspects, 267 (2005) 122-132.
M. Shribak, R. Oldenbourg, Techniques for Fast and Sensitive Measurements of Two-Dimensional Birefringence Distributions, Applied Optics, 42 (2003) 3009-3017.
A. Sengupta, A. Herminghaus, C. Bahr, Liquid crystal microfluidics: surface, elastic and viscous interactions at microscales, Liquid Crystals Reviews, 2 (2014) 73-110.
D. Voloschenko, O.P. Pishnyak, S.V. Shiyanovskii, O.D. Lavrentovich, Effect of director distortions on morphologies of phase separation in liquid crystals, Phys Rev E, 65 (2002) 060701.
D.C. Duffy, J.C. McDonald, O.J.A. Schueller, G.M. Whitesides, Rapid Prototyping of Microfluidic Systems in Poly(dimethylsiloxane), Analytical Chemistry, 70 (1998) 4974-4984.

Antonio Ramos, Electrohydrodynamic Pumping in Microsystems, in: A. Ramos (Ed.) Electrokinetics and Electrohydrodynamics in Microsystems, Springer Vienna2011, pp. 127-175.
T.H. Ware, M.E. McConney, J.J. Wie, V.P. Tondiglia, T.J. White, Voxelated liquid Crystal elastomers, Science, 347 (2015) 982-984.
S. Hernàndez-Navarro, P. Tierno, J. Ignés-Mullol, F. Sagués, Liquid-crystal enabled electrophoresis: Scenarios for driving and reconfigurable assembling of colloids, Eur. Phys. J. Spec. Top., 224 (2015) 1263-1273.
Green, Nicolas G., Dielectrophoresis and AC Electrokinetics, School of Electronics and Computer Science, University of Southampton, Electrokinetics and Electrohydrodynamics in Microsystems, CISM, (Udine 2011) 61-84.
W. Helfrich, Conduction-Induced Alignment of Nematic Liquid Crystals: Basic Model and Stability Considerations, The Journal of Chemical Physics, 51 (1969) 4092-4105.
C.A. Cartier, A.M. Drews, K.J.M. Bishop, Microfluidic mixing of nonpolar liquids by contact charge electrophoresis, Lab on a Chip, 14 (2014) 4230-4236.
A. Sengupta, S. Herminghaus, C. Bahr, Liquid crystal microfluidics: surface, elastic and viscous interactions at microscales, Liquid Crystals Reviews, 2 (2014) 73-110.
E.F. Carr, Influence of Electric Fields on the Molecular Alignment in the Liquid Crystal p-(Anisalamino)-phenyl Acetate, Molecular Crystals and Liquid Crystals, 7 (1969) 253-268.
Ivan I. Smalyukh et al., Optical trapping of director structures and defects in liquid crystals using laser tweezers, Optics Express 4359, vol. 15, No. 7 (Apr. 2007).
Oleg D. Lavrentovich et al., "Nonlinear electrophoresis of dielectric and metal spheres in a nematic liquid crystal," Nature, vol. 467, pp. 947-950, 2010.
Israel Lazo et al., Liquid crystal-enabled elctro-osmosis through spatial charge separation in distorted regions as a novel mechanism of electrokinetics, Nature Communications, 5, 2 pages, 2014.
Sergi Hernandez-Navarro et al., "AC electrophoresis of microdroplets in anisotropic liquids: transport, assembling and reaction," Soft Matter, 9, pp. 7999-8004, 2013.
H. Yoshida et al., "Three-dimensional positioning and control of colloidal objects utilizing engineered liquid crystalline defect networks," Nature Communications, 6, 2 pages, 2014.
Oleg Yaroshchuk et al., "Photoalignment of liquid crystals: basics and current trends," Journal of Materials Chemistry, 22, pp. 286-300, 2012.
William Thielicke et al,, "PIVlab—Towards User-friendly, Affordable and Accurate Digital Particle Image Velocimetry in MATLAB," Journal of Open Research Software, 2: e30, pp. 1-10, 2014.
Christopher Culbreath et al., "Note: Automated maskless micro-multidomain photoalignment," Review of Scientific Instruments, 82, pp. 126107-1 to 126107-3, 2011.
Abraham D. Stroock et al., "Chaotic Mixer for Microchannels," Science, Vo. 295, pp. 647-651, 2002.
S. V. Shiyanovskii et al., "Tensor and complex anchoring in liquid crystals," Physical Review E, vol. 62, No. 2, pp. R1477-R1480, 2000.
Kunihiro Ichimura, "Regulation of Liquid Crystalline Alignment by Photochromic Molecular Films," Photochemical Processes in Organized Molecular Systems, pp. 383-391, 1991.
David Therriault et al., "Chaotic mixing in three-dimensional microvascular networks fabricated by direct-write assembly," Nature Materials, 2, pp. 1-7, 2003.
T. Ishikawa et al., "Crossing of disclinations in nematic slabs," Europhysics Letters, 41, pp. 171-176, 1998.
M. C. Marchetti, "Hydrodynamics of soft active matter," Reviews of Modern Physics, vol. 85, pp. 1143-1189, 2013.

* cited by examiner

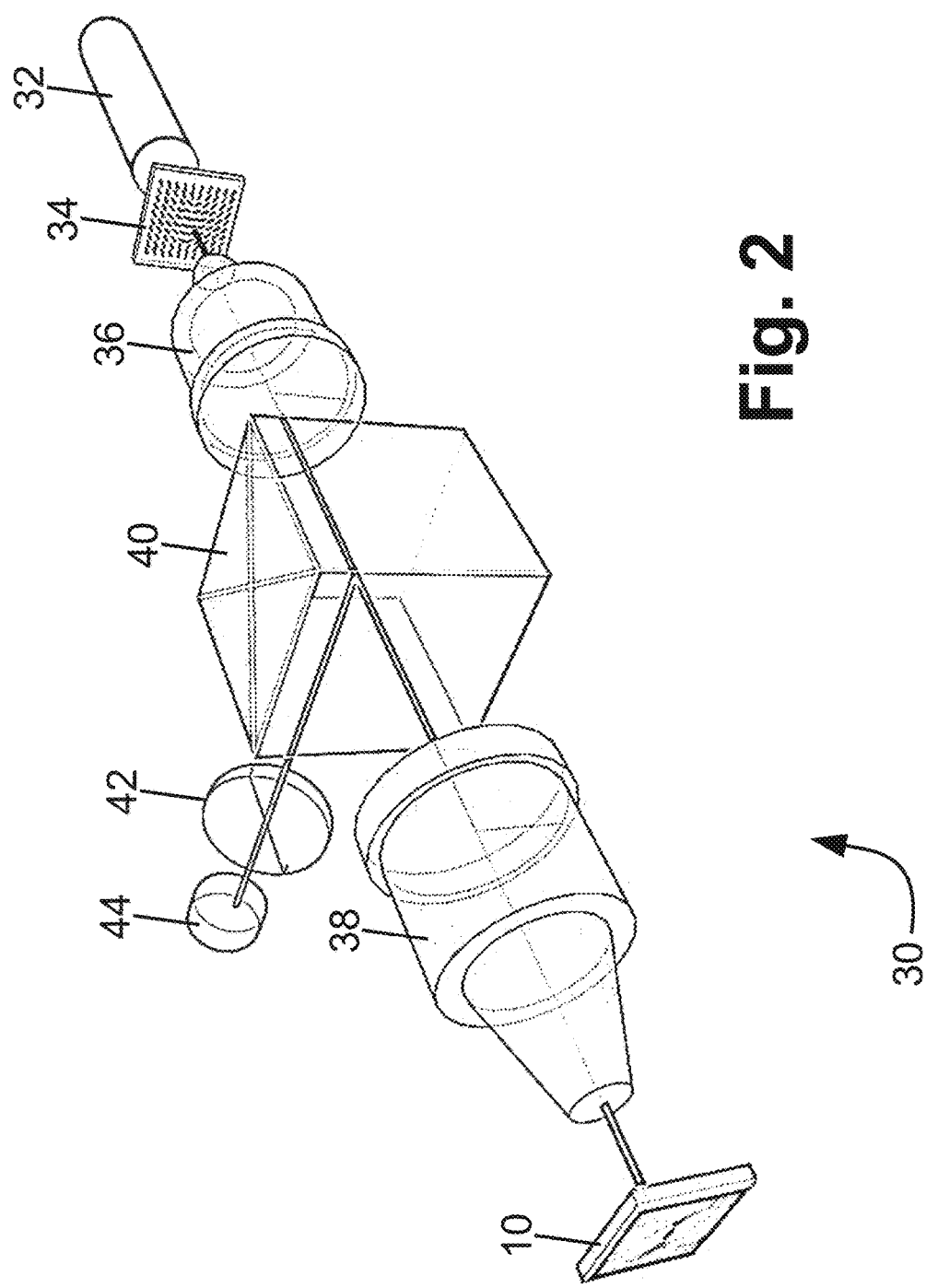

Parameters used in numerical simulations of electro-osmotic flows

| Parameter | Value | Description |
|---|---|---|
| $d$ | 50 $\mu$m | Defect separation |
| $T$ | 295 K | Room temperature |
| $\mu_\perp$ | $1.2 \times 10^{-19}$ m$^2$/V s | Mobility perpendicular to director |
| $\mu_\parallel$ | $1.7 \times 10^{-19}$ m$^2$/V s | Mobility parallel to director |
| $\varepsilon_\perp$ | 6 | Perpendicular dielectric constant |
| $\varepsilon_\parallel$ | 6 | Parallel dielectric constant |
| $E_0$ | 40 mV/$\mu$m | Electric field magnitude |
| $V_0$ | 30 V | Potential difference |
| $f$ | 5 Hz | Frequency of ac field |
| $n_0$ | $10^{19}$ m$^{-3}$ | Concentration of positive and negative ions in domain |
| $K_1$ | $5.3 \times 10^{-12}$ N | Splay elastic constant |
| $K_2$ | $2.2 \times 10^{-12}$ N | Twist elastic constant |
| $K_3$ | $7.45 \times 10^{-12}$ N | Bend elastic constant |
| $\alpha_1$ | $6.5 \times 10^{-3}$ Pa s | Leslie-Ericksen viscosity |
| $\alpha_2$ | $-77.5 \times 10^{-3}$ Pa s | Leslie-Ericksen viscosity |
| $\alpha_3$ | $-1.2 \times 10^{-3}$ Pa s | Leslie-Ericksen viscosity |
| $\alpha_4$ | $83.2 \times 10^{-3}$ Pa s | Leslie-Ericksen viscosity |
| $\alpha_5$ | $46.3 \times 10^{-3}$ Pa s | Leslie-Ericksen viscosity |

Fig. 3

LIQUID CRYSTALS WITH PATTERNED MOLECULAR ORIENTATION AS AN ELECTROLYTIC ACTIVE MEDIUM

This application claims the benefit of U.S. Provisional Application No. 62/259,190 filed Nov. 24, 2015 and titled "LIQUID CRYSTALS WITH PATTERNED MOLECULAR ORIENTATION AS AN ELECTROLYTIC ACTIVE MEDIUM" and claims the benefit of U.S. Provisional Application No. 62/403,918 filed Oct. 4, 2016 and titled "LIQUID CRYSTALS WITH PATTERNED MOLECULAR ORIENTATION AS AN ELECTROLYTIC ACTIVE MEDIUM". U.S. Provisional Application No. 62/259,190 filed Nov. 24, 2015 and U.S. Provisional Application No. 62/403,918 filed Oct. 4, 2016 are both hereby incorporated by reference in its entirety into the specification of this application. This invention was made with Government support under grant/contract no. DMR-1507637 and DMS-1434185 awarded by the National Science Foundation (NSF). The Government has certain rights in this invention.

BACKGROUND

The following relates to the fluid flow processing arts, mass transport arts, electro-osmotic, electrophoresis, and electrokinetic device arts, and related arts.

Electrokinetics relates to electrically driven mass transport, and is of technological importance in various forms. One electrokinetic process is the electrically driven flow of a fluid with respect to a solid surface, referred to as electro-osmosis. Another electrokinetic process is the electrically driven transport of particles in fluids, referred to as electrophoresis. A necessary condition of electrokinetics is separation of electric charges in space. Once separated, these charges can be carried by an applied electric field, thus producing electro-osmosis or electrophoresis.

A known approach for achieving charge separation at a solid-fluid interface is through dissociation of molecular groups and the formation of electric double layers. Another approach is to separate charges by the applied electric field, but this is applicable only to highly polarizable solid components. In an isotropic electrolyte fluid, the solid component mediates separation of charges, and the fluid supplies counterions to complete the double layer buildup.

These approaches have substantial disadvantages. For example, to achieve electrophoresis by these mechanisms the transported particles must be polarizable, e.g. an ionic compound such as a salt that can be separated into cation and anion components. This limits the range of particles that can be subjected to electrophoresis by these mechanisms in terms of surface charge magnitude, polarizability, shape asymmetry, and other properties.

BRIEF SUMMARY

In some illustrative embodiments, a transport device comprises: a fluid cell comprising parallel substrates; an anisotropic electrolyte disposed in the fluid cell; and electrodes configured to apply an AC electric field to the anisotropic electrolyte disposed in the fluid cell. A substrate of the fluid cell includes a pattern that induces a director distortion pattern in the anisotropic electrolyte disposed in the fluid cell. The director distortion pattern has a gradient configured to induce electrokinetic flow of the anisotropic electrolyte in the fluid cell in response to the AC electric field applied by the electrodes. Cargo, such as particles, gas bubbles, or fluid, is dispersed in the anisotropic electrolyte and transported in the fluid cell by the induced electrokinetic flow of the anisotropic electrolyte. The induced electrokinetic flow may be linear, curvilinear, or circular so as to induce mixing, depending on the director pattern. The director pattern might be non-singular (defect-free) or may contain defects such as disclinations that produce pumping effects and can trap cargo at a core of the disclination.

In some illustrative embodiments, a transport method is disclosed. A director distortion pattern is induced in an anisotropic electrolyte disposed in a fluid cell. The induced director distortion pattern has a gradient configured to induce electrokinetic flow of the anisotropic electrolyte. An AC electric field is applied to the anisotropic electrolyte disposed in the fluid cell whereby electrokinetic flow of the anisotropic electrolyte is induced. The director distortion pattern may be induced by forming a pattern on a substrate of the fluid cell, the pattern inducing the director distortion pattern. In some illustrative embodiments, the pattern on the substrate is formed by performing patterned photoalignment of a photosensitive layer disposed on the substrate using a plasmonic mask with nanoslits.

BRIEF DESCRIPTION OF THE DRAWINGS

FIG. 2 diagrammatically shows a photopatterning optical exposure setup for forming a predistorted director pattern of the microfluidic chamber of FIG. 1.

FIG. 3 lists the parameters used in numerical simulations reported herein.

FIGS. 10a and 10b illustrate transport of polystyrene spheres; FIGS. 10c and d illustrate transport of air bubbles; FIGS. 10e and 10f illustrate transport of water.

FIG. 11a shows the Y-junction with a photo-imprinted mixing pad. FIG. 11b shows PolScope texture of the mixing pad. FIG. 11c shows velocity maps within the mixing pad. FIG. 11d shows a comparison of mixing efficiencies of passive diffusion (E=0) and liquid-crystal-enabled electrokinetics (LCEK) driven diffusion (E=40 mV/μm). FIG. 11d insets show the fluorescence microscopy textures of the mixing pad with the exposure time interval 550 s after the start of mixing.

DETAILED DESCRIPTION

Figure 1:
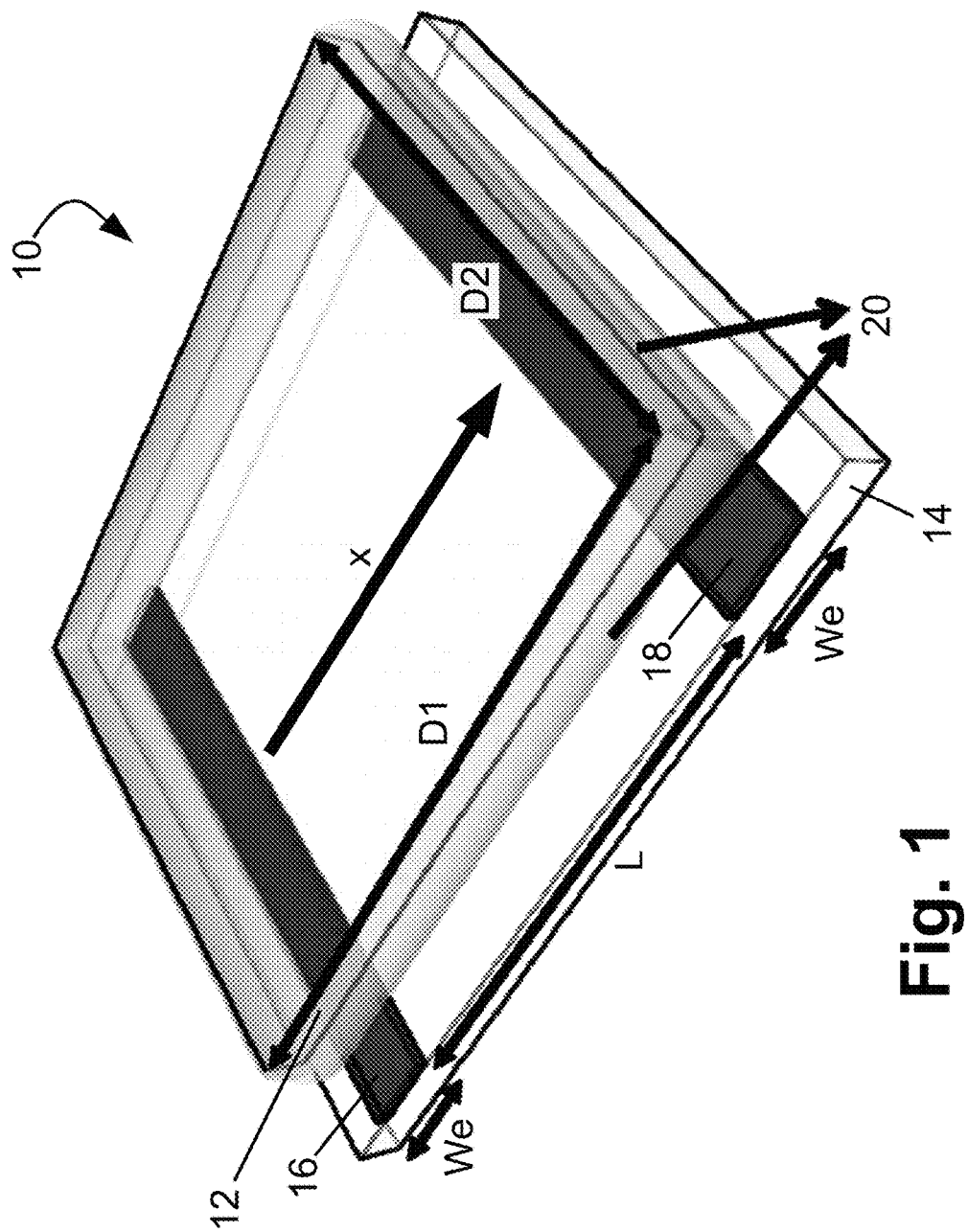
FIG. 1 diagrammatically shows a microfluidic chamber as disclosed herein.

Disclosed herein are versatile approaches to generating electrokinetic effects by using a liquid crystal (LC) with surface-patterned molecular orientation as an electrolyte. The patterned molecular orientation may be described by spatial variations of the director $\hat{n}(r)$. By producing a desired pattern of $\hat{n}(r)$, for example by photo-alignment of substrates bounding a LC cell, a desired electrokinetic flow path can be defined. The substrate-imposed pattern imposes director distortions extending a substantial distance into the LC bulk and possibly extending through the entire LC bulk, because of the elastic nature of the LC orientational order. As disclosed herein, in the presence of a uniform alternating current (ac) electric field, the spatially varying molecular orientation produces space charge that triggers streaming flows of the LC. The ensuing electrokinetics can transport solid, fluid, and even gaseous inclusions along a predesigned trajectory. The patterned LC electrolyte represents an active form of matter in which the energy input that drives the system out of equilibrium is localized at the gradients of the orientation order of the LC medium rather than at the particles embedded in the LC medium. Since the source of activity is rooted in the properties of the LC medium, the approach removes many limitations imposed by isotropic electrolytes on the properties of electrokinetically active interfaces and particles in them (such as the magnitude of surface charge, polarizability, shape asymmetry, etc.).

The disclosed electrokinetic approach is referred to herein as substrate-controlled liquid-crystal-enabled electrokinetics (LCEK), and is explained in greater detail as follows. LCs are anisotropic electrolytes, in that the electric conductivity $\sigma_\parallel$ measured along the average molecular orientation $\hat{n}$ is usually higher than the conductivity $\sigma_\perp$ measured along the direction perpendicular to $\hat{n}$. This anisotropy gives rise to the Carr-Helfrich effect of destabilization of a uniformly aligned LC cell, $\hat{n}(r)$=const. In the disclosed approach for achieving an electrokinetic effect, the starting point is a LC with a predistorted director pattern $\hat{n}(r) \neq$ const imposed by designed LC cell substrates. The applied electric field E moves charges of opposite signs along the curved director lines defined by the imposed pattern $\hat{n}(r) \neq$ const, accumulating the charges of different charge polarities in different regions of the LC bulk. The gradients of the director thus lead to the electric field E creating a nonvanishing volume density of charges $\rho(r)$. This volume density of charges depends on the conductivity, and on the dielectric permittivity of the LC and its anisotropy. The electric field acts on the space charge $\rho(r)$, creating flows of the LC. These flows carry particles dispersed in the LC, since the separation of charges occurs in the bulk of the LC medium rather than at (or near) the particle's surface, as in the case of existing electrokinetic approaches that employ electric double layers around particles in isotropic electrolytes and charges separated by director distortions near the colloidal particles placed in an otherwise uniform LC.

In illustrative embodiments, the bulk director distortions operating to provide substrate-controlled LCEK are achieved through patterned photoalignment. To define the flow pattern for LCEK, the molecular orientation should change from point to point in pattern. To precisely implement the desired $\hat{n}(r)$ pattern defining the flow, methods of surface alignment such as buffing or rubbing of the substrates with the tip of a cantilever in an atomic force microscopy setup are not practical for large-scale manufacturing. In the illustrative embodiments, a modified version of photoalignment is used, in which the cell substrates are irradiated through plasmonic masks with nanoslits. When such a mask is illuminated with nonpolarized light, the slits transmit a polarized optical field that is projected onto a photoaligning layer. The polarized optical field projected onto the photoaligning layer imposes the desired director field $\hat{n}(r)$ at the substrate and in the adjacent LC.

With reference to FIG. 1, an illustrative assembled microfluidic chamber 10 is shown. The chamber 10 is bounded by two glass plates 12, 14. One glass plate 12 is a bare glass, and the other glass plate 14 has stripe indium tin oxide (ITO) electrodes 16, 18 separated by a gap L, where L=10 mm in some illustrative embodiments. In an illustrative embodiment, the glass plate 12 has a dimension D1 of 15 mm parallel with the gap L and a dimension D2 of 10 mm transverse to the gap L, and the electrodes 16, 18 has a width We of 3 mm. Both glass plates 12, 14 are coated with the photoalignment material on their inside surfaces (i.e. the surfaces that contact the liquid crystal material. The width of each electrode 16, 18 is 3 mm. After the chamber is filled with the liquid crystal, it is sealed by an epoxy 20.

Experiments employing the microfluidic chamber 10 of FIG. 1 were performed using the following materials and parameters. A nematic LC with zero dielectric anisotropy ($|\Delta\varepsilon| \leq 10^{-3}$) was formed by two components: MLC7026-000 and E7 (both from EM Industries) in weight proportion 89.1:10.9. Zero dielectric anisotropy simplifies the experiments and analysis although it is not a necessary requirement to trigger LCEK. The concentration of ions in the mixture was $n_0 \approx 10^{19}$ ions·m$^{-3}$. The LC was filled by capillary action between the two glass plates 12, 14 with the predesigned alignment pattern; both top and bottom plates 12, 14 were treated through a photomask in the assembled state, and thus the two photoinduced patterns are the same and establish the distorted director in the LC bulk. The electric field (root-mean-square amplitude E=40 mV/μm, frequency 5 Hz) was applied in the plane of the cell along the x axis (labeled x in FIG. 1) by the two indium tin oxide (ITO) stripe electrodes 16, 18, separated by the distance L of 10 mm. The LC cell was sealed by the epoxy glue 20. All experiments were performed at 22° C.

To form the patterned alignment layers, the photosensitive material Brilliant Yellow (BY) (from Sigma-Aldrich) was used without further purification. BY was mixed with N,N-dimethylformamide (DMF) solvent at 1 wt % concentration. In order to improve the stability of BY, the reactive mesogen RM257 was mixed with DMF at the concentration 0.2 wt % and then mixed with the solution of BY in DMF (1 wt %) in the ratio 1:1. After vortexing for 1 min, the solution was spin coated onto two cleaned glass plates, including both the bare glass plate 12 and the glass plate 14 with the two patterned ITO electrodes 16, 18 separated by the gap L of 10 mm. The glass plates 12, 14 were baked at 95° C. for 30 min. The two glass plates 12, 14 were assembled in a parallel fashion with a gap of 50 μm between them, set by spherical silica spacers (not shown in FIG. 1). The fabricated chambers are placed in an optical exposure system and exposed for 30 min. The cell was then filled with the liquid crystal by capillary action. The exposed BY alignment layers align the LC director in the direction parallel to the long side of the slits in the photomask. Since the plates were exposed simultaneously, the photoinduced pattern of the director was the same on both surfaces.

With reference to FIG. 2, the photopatterning optical exposure setup 30 is shown. In this setup, a light beam from an illumination lamp 32 passes through a photomask 34 with a predesigned patterns of slits for defining the desired pattern, and becomes polarized. The pattern image is then focused on the inner surfaces of the microfluidic LC chamber 10 by the combination of two objective lenses 36, 38. In the performed experiments, the illumination lamp 32 was an X-Cite 120 illumination system, and goes through the designed patterns of the photomask 34. Masks 34 with experimental patterns were made of aluminum films of 150 nm thickness, perforated with rectangular nanoslits, each of a length 220 nm and width 120 nm. After passing through the mask, the initially non-polarized light beam from the illumination lamp 32 becomes polarized. The pattern images are then focused on the microfluidic chamber 10 by the combination of two objective lenses 36, 38. In the setup of FIG. 2, a beam splitter 40 and imaging lens 42 enables the patterns on the chamber surfaces to be checked by a CCD camera 44 (a Scopetek CCD camera was used in the experiments). After the director pattern images are focused on the surfaces with photoalignment materials, the exposure starts. The exposure time in the illustrative experiments was 30 min. The director was confined to the plane parallel to the bounding plates 12, 14 of the cell. The director pattern was imprinted onto a square region of area 1 mm$^2$; the square was surrounded by the uniformly aligned nematic n̂=(1,0,0), extending over large distances of 1 cm.

Various experiments were performed on microfluidic chambers 10 assembled as just described. The testing apparatuses are described next.

The velocities of the electro-osmotic flows were measured by videomicroscopy using a Nikon Eclipse E600 microscope with a motorized stage (Prior Scientific) equipped with a CARV confocal imager (BD Biosciences) and Photometrics Cascade 650 video camera. The fluorescent illumination system X-Cite 120 was used with the excitation wavelength of 480 nm and emission wavelength of 535 nm. The LC is doped with a small amount (~0.01 wt %) of tracers, representing fluorescent polystyrene spheres (Bangs Laboratories) of diameter 2R=0.2 µm. The small size of the tracers allows for elimination of the potential influence of dielectrophoretic effects. The microscope was focused at the middle plane of the cell. The tracers caused no visible distortions of the director and are practically nonpolarizable. The fluorescent signal of tracers was recorded as a TIFF image with a typical exposure time $\Delta\tau$=325 ms. The flow trajectories were established using the software package MetaMorph (Molecular Devices) to superimpose over 1500 images to render a single composite picture. The experimental flow velocity fields were obtained using the microparticle imaging velocimetry (µPIV) software PIV-LAB operated in MATLAB version R2010b which correlates the position of tracers in consecutive images.

The director fields produced by photopatterning were established using a polarizing microscope (Nikon E600) equipped with the Cambridge Research Abrio LC-PolScope package. This system uses monochromatic illumination at 546 nm and maps the optical retardance and orientation of the optical axis.

Some microfluidic devices (i.e. microfluidic chambers) were fabricated for micromixing. In these devices, a photoresist, SU-8 2025 (MicroChem) was spin coated onto the cleaned glass substrates at 500 rpm for 30 s and 1500 rpm for 30 sec to create a film with the thickness 50 µm that will be the depth of the channels. After photoresist coating, the substrates were prebaked at 65° C. for 2 min and then at 95° C. for 8 min. The inlets of the devices have a width of 500 µm and the main channel has a width of 1 mm. The angle between the inlets is 40°. This microchannel design is patterned in the SU-8 films by using a maskless photopatterning system with the digital micromirror devices as dynamic masks. After UV exposure for 30 sec, the substrates were postbaked at 65° C. for 1 min and at 95° C. for 5 min. After development in SU-8 developer (MicroChem) for 5 min, the substrates were rinsed with isopropanol for 1 min to form microchannels. The substrate with the microfluidic channel was spin coated with BY-RM257 mixture at 1500 rpm for 30 sec and baked at 95° C. for 30 min. Two holes were drilled in the substrate with a microabrasive sand blaster (Problast by Vaniman Manufacturing), in order to provide the inlets for the fluids. This substrate was then covered by another glass substrate with patterned ITO electrodes and also coated with the same photoalignment material. The mixing microfluidic chamber was photoaligned as described with reference to FIG. 2.

To characterize the micromixing efficiency, an approach was used that is based on the standard deviation in the intensity of optical microscopy images of the mixing chamber. The comparison was made for two different modes of mixing, by passive diffusion and by LCEK flows. The time development of mixing was tracked by taking 3000 images by videomicroscopy. Each image contains N=653×492=321,276 pixels of variable intensity $I_i$, as determined by fluorescent particles. The value of $I_i$ is dimensionless, being normalized by the maximum possible intensity $I_{max}$. In addition to the intensity of each pixel $I_i$, the average intensity of each image, $$I_{ave} = \frac{1}{N}\sum_{i=1}^{N} I_i,$$

was also calculated. The standard deviation is defined as $$\delta = \sqrt{\frac{1}{N}\sum_{n=1}^{N}(I_i - I_{ave})^2}.$$

In the unmixed state, the mixing pad was divided into two parts of equal area, one with the maximum fluorescent intensity $I_{max}$=1 and the other with the minimum intensity $I_{min}$=0; the average intensity is $I_{av}$=0.5, so that:

$$\delta = \delta_0 = \sqrt{\frac{(I_{max} - I_{ave})^2 + (I_{min} - I_{ave})^2}{2}} = \frac{1}{2}$$

In the completely mixed state, the fluorescent intensity $I_i$=$I_{ave}$, so that $$\delta = \sqrt{\frac{1}{N}\sum_{i=1}^{N}(I_{av} - I_{ave})^2} = 0.$$

Numerical simulations of the electro-osmotic flows were also performed as follows. A transport model was developed to simulate electro-osmotic flows for different photopatterned arrays, using the Leslie-Ericksen hydrodynamics. The model includes anisotropic mobilities $\mu_{ij}=\mu_\perp\delta_{ij}+\Delta\mu n_i n_j$ where the anisotropic contribution is $\Delta\mu=\mu_\parallel-\mu_\perp$. We consider positive and negative ions of equal concentration, $n_0\approx10^{19}$ ions·m$^{-3}$. The model was solved numerically using the finite-element software package COMSOL in two dimensions, with the parameters of the nematic cell, applied field amplitude, and frequency being the same as those used in laboratory experiments, namely, E=40 mV/µm and 5 Hz. FIG. 3 lists the parameters used in these numerical simulations. The domain of calculations consists of a square $S_0$ with the side $L_{domain}$=750 µm, containing a smaller square $S_1$ with the side length 150 µm. The entire domain contains 6294 elements, with $S_1$ more finely meshed than the rest of the domain $S_0$. The smaller square $S_1$ contains a free triangular mesh with maximum linear size 4.02×10$^{-6}$ m and minimum size 1.5×10$^{-8}$ m. Outside of $S_1$, the mesh contains thin quadrilateral boundary layer elements near the edges of $S_0$, with the rest of the domain containing free triangular elements of maximum linear size 1.11×10$^{-4}$ m and minimum size 3.75×10$^{-7}$ m. No-slip boundary conditions were imposed on the boundaries of the $S_0$ domain. In the resulting simulated electro-osmotic flow patterns, both the charge distribution and the velocity field oscillate in time (as a result of the ac driving field); however, the direction of the velocities remains constant. The latter fact reflects the LCEK mechanism, according to which the driving force of electro-osmosis represents the product of the field-induced charge and the field itself, i.e., the force is proportional to the square of the electric field. The pattern symmetry and the order of magnitude of the circulated velocity are quite close to those measured experimentally, with a maximum at about 7 μm/s.

A condition for electrokinetic motion of the LC is spatial separation of charges. In the following, the spatial charge created by a non-uniform director field in the presence of an electric field is derived using Maxwell's equations.

In the disclosed substrate-controlled LCEK, the space charge is induced by the electric field because of the preimposed director deformations. The space charge density ρ is derived in the following for the director field distorted in the xy plane, n̂={cos α(x,y), sin α(x,y), 0}, where α is the angle between the director n̂ and the x axis. The starting point is Maxwell's equation for the magnetic field H:

$$\operatorname{curl} H = \frac{\partial D}{\partial t} + J \quad (1)$$

Consider a low-frequency harmonic field $E(t)=Ee^{-i\omega t}$ that creates the current density $J(t)=Je^{-i\omega t}=\sigma E e^{-i\omega t}$ and the electric displacement $D(t)=De^{-i\omega t}=\varepsilon_0 \varepsilon E e^{-i\omega t}$; here $\sigma = \sigma_\perp I + \Delta\sigma \hat{n} \otimes \hat{n}$ and $\varepsilon = \varepsilon_\perp I + \Delta\varepsilon \hat{n} \otimes \hat{n}$ are, respectively, the conductivity and dielectric tensors in the laboratory frame, $\Delta\varepsilon = \varepsilon_\parallel - \varepsilon_\perp$ is the dielectric anisotropy, and $\otimes$ is the external product of two vectors. The operation's result is a tensor with components $[\hat{n} \otimes \hat{n}]_{ij} = n_i n_j$. It is assumed here that the diagonal components $\sigma_\parallel$ and $\sigma_\perp$ of the conductivity tensor and the diagonal components $\varepsilon_\parallel$ and $\varepsilon_\perp$ of the dielectric tensor are frequency independent. Equation (1) can be rewritten as $$\operatorname{div}\left(\frac{\partial D}{\partial t} + J\right) = \operatorname{div} \tilde{\sigma}(\omega) E = 0 \quad (2)$$

where $\tilde{\sigma} = \sigma - i\omega\varepsilon_0 \varepsilon$ is the effective conductivity tensor. For low frequency $$\omega \ll \frac{\sigma_\perp}{\varepsilon_0 \varepsilon_\perp} \ll c/L$$

(where c is the speed of light and L is the distance between the electrodes), $\tilde{\sigma} \approx \sigma$ and $E = -\nabla V$, where the potential V obeys the equation div(σ∇V)=0, or:

$$\sigma_\perp \nabla^2 V + \Delta\sigma \operatorname{div}[(\hat{n} \cdot \nabla V)\hat{n}] = 0 \quad (3)$$

and thus the charge density ρ=divD reads:

$$\rho = -\varepsilon_0\left(\Delta\varepsilon - \frac{\varepsilon_\perp \Delta\sigma}{\sigma_\perp}\right) \operatorname{div}(\hat{n} \cdot \nabla V)\hat{n} \quad (4)$$

Consider the external field $E_0$ applied along the x axis and assume a weak anisotropy of conductivity, $\Delta\sigma \ll \sigma_\perp$. The electric field acting on the LC can be represented as $E=\{E_0+\tilde{E}_x(x,y), \tilde{E}_y(x,y)\}$, where $\tilde{E}_x(x,y)$ and $\tilde{E}_y(x,y)$ are small corrections caused by the director inhomogeneity that satisfy Equation (4). In the first perturbation order:

$$\sigma_\perp\left(\frac{\partial \tilde{E}_x(x,y)}{\partial x} + \frac{\partial \tilde{E}_y(x,y)}{\partial y}\right) + \Delta\sigma E_0\left(\cos 2\alpha \frac{\partial \alpha}{\partial y} - \sin 2\alpha \frac{\partial \alpha}{\partial x}\right) = 0 \quad (5)$$

The electric field E creates the spatially varying charge density:

$$\rho = \varepsilon_0(\Delta\varepsilon - \varepsilon_\perp \Delta\sigma/\sigma_\perp) E_0\left(\cos 2\alpha \frac{\partial \alpha}{\partial y} - \sin 2\alpha \frac{\partial \alpha}{\partial x}\right) \quad (6)$$

The field-induced charge density ρ is being acted upon by the applied electric field, thus creating a force density $f = \rho E_0 \propto E_0^2$ that causes the flow of the LC controlled by the surface-imposed director pattern. Note that Equation (6) shows the space charge being dependent on both the conductivity anisotropy Δσ and the dielectric anisotropy Δε; either one of them or both can lead to charge separation. In the experimentally studied material, there is no dielectric anisotropy; thus in what follows, Equation (6) is used with Δε=0. This choice simplifies the analysis by eliminating the dielectric torques on the director. However, nonzero dielectric anisotropy can be used to create, enhance, or control the space charge, depending on the sign of Δε, as evident from Equation (6).

In the following, experimental results obtained using the foregoing experimental tests presented.

Figure 4:
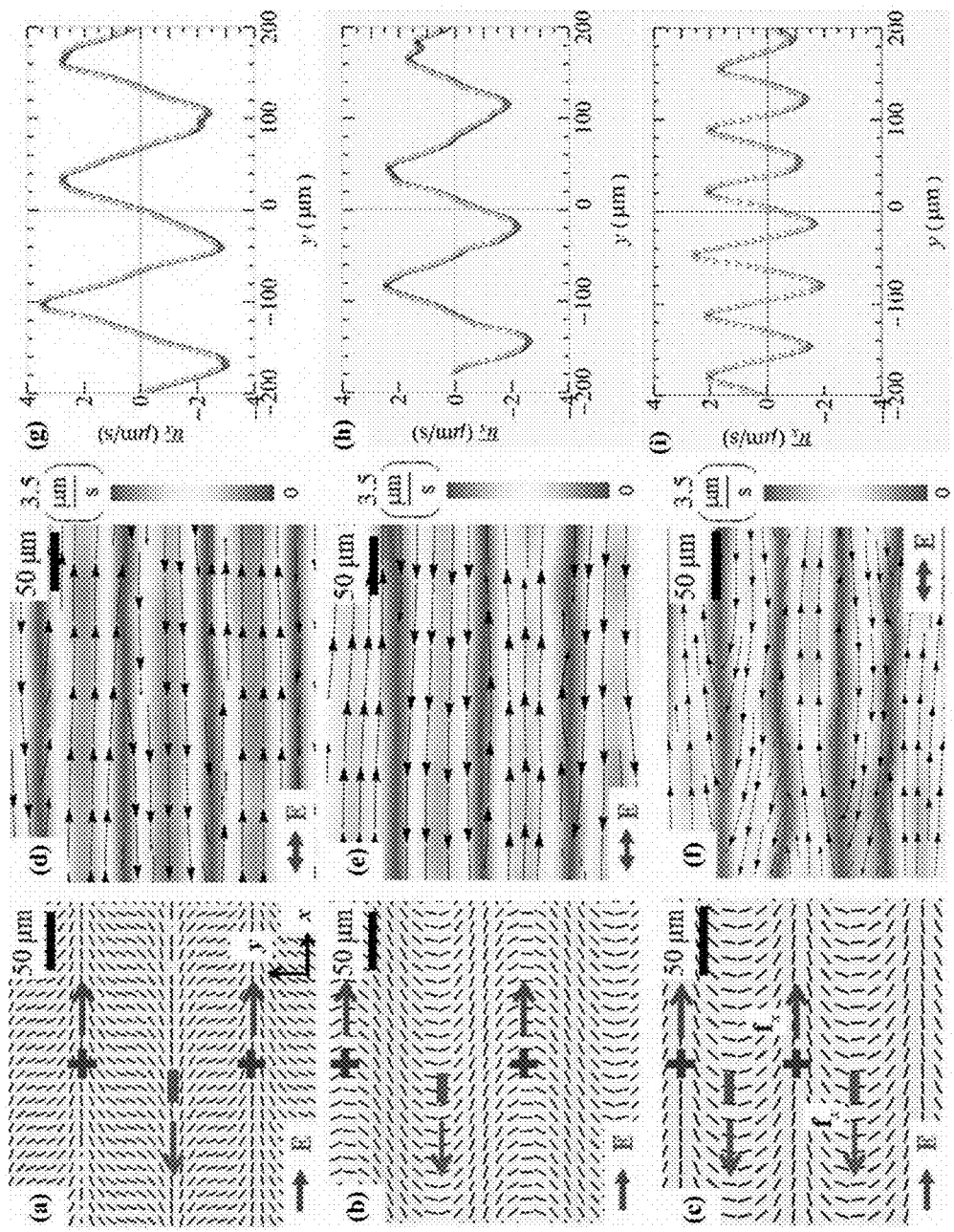
FIGS. 4-9 illustrate simulation and experimental results as described herein.

With reference to FIG. 4, electrokinetic flows in LC electrolytes with one-dimensionally periodic director patterns are described. FIGS. 4(a), 4(b), and 4(c) show three different examples of one-dimensional periodic patterns of the director n̂=(n_x, n_y, 0)={cos α(y), sin α(y), 0}, in the photoaligned nematic cell. The patterns are designed as:

$$\alpha(y) = T(y) \quad (7a)$$

$$\alpha(y) = \frac{\pi}{2} + T(y) \quad (7b)$$

$$\alpha(y) = \pi(1 - y/l) \quad (7c)$$

in FIGS. 4(a), 4(b), and 4(c), respectively, where $$T(y) = \arcsin\left(\sin\frac{\pi y}{l}\right)$$

is the triangle wave of the amplitude π/2 and period l. FIGS. 4(a), 4(b), and 4(c) show PolScope textures of nematic cell with surface-imposed director patterns described by Equations (7a)-(7c), respectively, with "+" and "−" showing the charges separated by the electric field of the shown polarity. Reversal of the field polarity reverses the polarity of the charges but the driving Coulomb force remains the same. Note that finite azimuthal anchoring reduces the actual amplitude to about 0.4π in FIGS. 4(a) and 4(b).

In the absence of an electric field, the ions are distributed homogeneously in the sample. When the electric field is applied along the x axis, $E=(E_0, 0)$, it separates the positively and negatively charged ions along the y axis, by moving them along the "guiding rail" of the director. For example, in FIG. 4(c), as can be seen for the shown direction of the electric field, the anisotropic conductivity $\Delta\sigma = \sigma_\parallel - \sigma_\perp > 0$ helps to accumulate positive charges in the regions with the "horizontal" director, $n_x=1$, $n_y=0$, and the negative ones in the regions with $n_x=0$, $n_y=1$. The general expression for the space charge density given by Equation (6) can be applied to each of the three patterns in Equation (7) to find the corresponding one-dimensionally varying function ρ(y) (neglecting at the moment edge effects, as the length of stripes is much larger than their width). For example, for Equation (7c) and FIG. 4(c), with α=π(1−y/l) where l is the period, according to Equation (6) in the approximation of low frequency of the field the charge density is:

$$\rho(y) = \frac{\pi \varepsilon_0 \varepsilon_\perp}{l} \frac{\Delta \sigma}{\sigma_\perp} \cos\left(\frac{2\pi y}{l}\right) E_0 \qquad (8)$$

The space charge is steady, as long as there are predesigned director distortions, i.e., the spatial derivatives ∂α/∂x and ∂α/∂y are nonzero.

Once the charges are separated, the periodic bulk force $f_x(y)=\rho E_0 \propto E_0^2$ acting on the ionic clouds causes spatially periodic LC electrokinetic flow. FIGS. 4(d), 4(e), and 4(f) show LC flow velocity maps caused by an ac field directed along the horizontal x axis for the cases of Equations 7(a)-7(c) respectively. FIGS. 4(g), 4(h), and 4(i) plot averaged x component of the nematic velocity versus the distance along the y axis for the cases of Equations 7(a)-7(c) respectively. Since the force $f_x$ is proportional to $E_0^2$, the flow does not depend on the field polarity. Reversing the polarity of E reverses the sign of ρ but the product ρE remains unchanged. This feature allows use of an ac field with zero average to produce electrokinetic flow. An advantage of ac driving is that the electrokinetic flows are persistent as long as the field is applied, and there are no detrimental electrode effects such as field screening and chemical reactions which are known to occur in the direct current driving case.

The predesigned director pattern in FIGS. 4(a), 4(b), and 4(c) controls many parameters of the ensuing LCEK flows, such as the viscous resistance to the flow. For example, the pattern in FIGS. 4(a) and 4(d) causes the maximum driving force to be directed along n̂; the flow experiences a relatively low effective viscosity $\eta_\parallel$. In FIGS. 4(b) and 4(e), the flow is mostly perpendicular to n̂, with a higher effective viscosity, $\eta_\perp > \eta_\parallel$, which results in slower velocities. Namely, the maximum amplitudes of velocities are 3.5 μm/s in FIG. 4(g), 2.6 μm/s in FIG. 4(h), and 2.5 μm/s in FIG. 4(i). Note that in the case of FIG. 4(c), the flows are less regular than in FIGS. 4(a) and 4(b).

A principal difference between the classic electroconvection phenomena described by the Carr-Helfrich model and the electrokinetics of the disclosed LCEK is here noted. In the Carr-Helfrich effect, the LC is aligned uniformly and the director distortions appear as a result of charge separation at director fluctuations. The director distortions usually adapt a form of "anomalous" reorientation, linear rolls, and a two-dimensional array of vortices, determined by the balance of electrohydrodynamic and elastic forces. By contrast, in the LCEK approach the principal director distortions are predesigned by surface alignment even before the electric field is applied. The concrete shape of these distortions determines the patterns of charge separation and controls the electrokinetic flows when the electric field is applied.

Furthermore, the patterns in FIGS. 4(a) and 4(b) pump an equal amount of LC to the left- and right-hand sides; the corresponding velocity profiles shown in FIGS. 4(d) and 4(e) are symmetric, with zero time average. In FIGS. 4(g) and 4(h) are presented the dependencies of the averaged x component of the velocity $$\bar{u}_x(y) = \frac{1}{n}\sum_{i=1}^{n} u_x(x_i, y)$$

on the distance measured along the y axis, where n=200 and $u_x(x_i, y)$ is the local velocity component along the x axis, known from the experiment in FIGS. 4(d) and 4(e). The maximum positive and negative values of the velocity $\bar{u}_x(y)$ are practically the same, as seen in FIGS. 4(g) and 4(h). Moreover, the net volumetric flow per unit time calculated for FIGS. 4(g) and 4(h) as $$Q_x = \frac{2}{3}h \int_{-y_0}^{y_0} \bar{u}_x(y)\,dy,$$

where $y_0=200$ μm and h=50 μm is the cell thickness, is practically zero: its deviation from the total volumetric flow defineu as $$Q_{x,total} = \frac{2}{3}h \int_{-y_0}^{y_0} |\bar{u}_x(y)|\,dy$$

is less than 1%. It can be concluded that the patterns in FIGS. 4(a) and 4(b) produce no pumping of the LC along the horizontal axis, as expected from the left-right symmetry of these patterns.

In contrast, the asymmetric pattern shown in FIG. 4(c) produces a net pumping of the LC to the right-hand side, as the overall velocity of flow to the right is higher than that to the left (see FIG. 4(i)), and does not average to zero when integrated over the y coordinate. The volumetric flow $Q_x$ per unit time calculated as above is significant, being about 10% of $Q_{x,total}$. The continuity of the flow is provided by the backflow of the LC from right to left in the homogeneous part of the sample, above and below the patterned area. This can be verified by observing the movement of a LC in a cell in which the patterned region occupies only a fraction of the entire area.

Results for electrokinetic flows in patterned LC electrolytes with topological defects are next described. In classic linear electrokinetics, the fluid velocity u is proportional to the electric field and the resulting flows are irrotational, ∇×u=0. For practical applications such as mixing, it is desirable to trigger flows with vortices. Vortices are readily produced in the patterned LC cells, by using localized surface patterns, for example, with topological defects. The topological defects offer another degree of freedom in manipulating colloids as they can be used for entrapment and release.

Director patterns with pairs of disclinations of strength (m=½,−½) and triplets such as (m=−½,1,½) and (m=½,−1,½) are created following the general form $n_x=\cos\alpha(x,y)$, $n_y=\sin\alpha(x,y)$, where:

$$\alpha(x, y) = m_1 \tan^{-1}\left(\frac{y}{x+d}\right) + m_2 \tan^{-1}\left(\frac{y}{x}\right) + m_3 \tan^{-1}\left(\frac{y}{x-d}\right) \qquad (9)$$

Here d is the distance between the cores of two neighboring defects. In all cases, the total topological charge $\Sigma_i m_i$ is zero, which allows one to smoothly embed the distorted pattern into an otherwise uniform director field. The charge (strength) m is determined by how many times the director rotates by the angle $2\pi$ when one circumnavigates the defect once. In the case of pairs, $m_1 = -m_2 = \frac{1}{2}$ and $m_3 = 0$. In the case of triplets, $m_1 = m_3 = -\frac{1}{2}$ and $m_2 = 1$. Equation (9) follows the principle of superposition valid for a director field in a one-constant approximation. These patterns are used to produce the pattern of slits in the photomask 34 and then are reproduced as the true director field in the assembled and photoaligned LC chambers.

Figure 5:
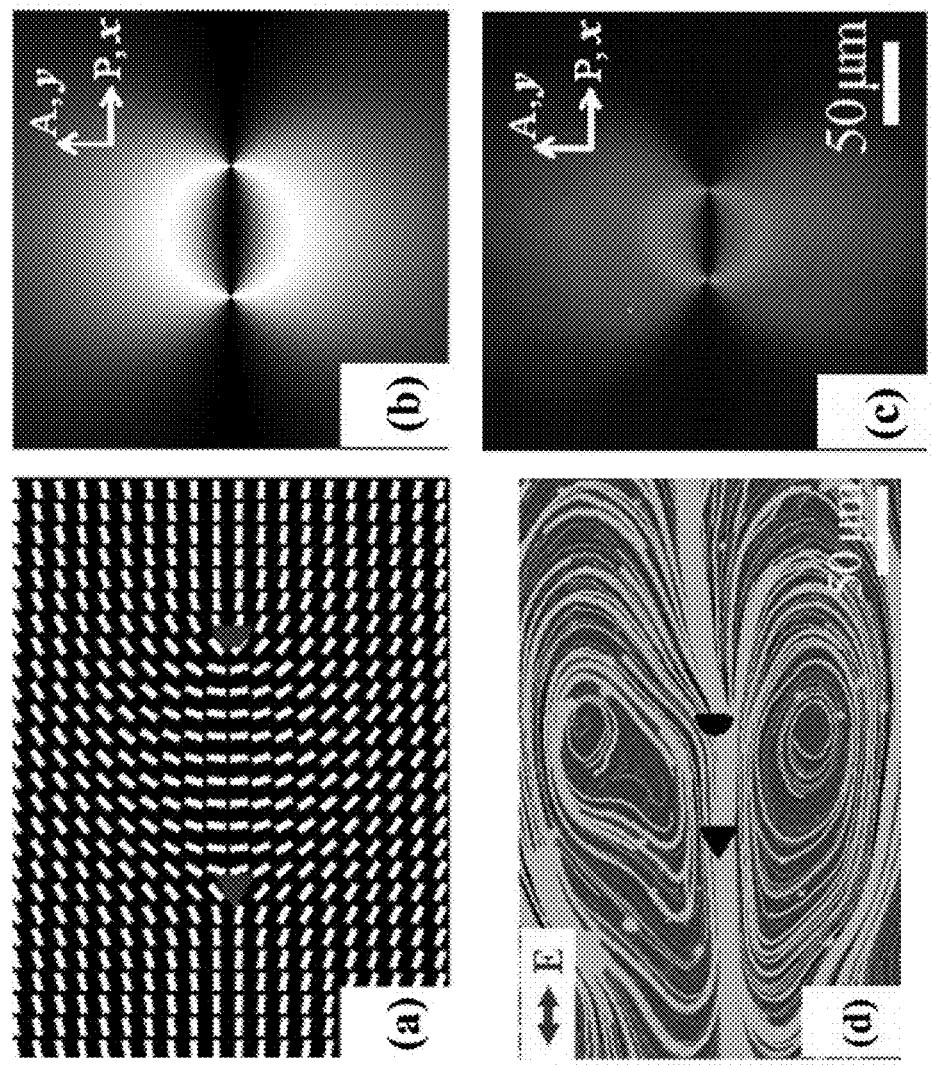

FIG. 5 shows the pattern of slits with a pair of half-integer defects and the main effects it produces in the assembled and photoaligned LC chamber, namely, the distorted director field with two disclinations of half-integer strength (FIG. 5(c)), and the two-vortex electro-osmotic flow patterns visualized by fluorescent markers (FIG. 5(d)). FIG. 5 shows results for a disclination pair ($-\frac{1}{2}, \frac{1}{2}$) pattern. FIG. 5(a) shows the designed ($-\frac{1}{2}, \frac{1}{2}$) director slits pattern; the disclination $-\frac{1}{2}$ core is marked by a triangle and the $\frac{1}{2}$ core is marked by a semicircle. FIG. 5(b) shows simulated polarizing microscopy texture of ($-\frac{1}{2}, \frac{1}{2}$) disclination pair. FIG. 5(c) shows experimental polarizing microscopy texture of the ($-\frac{1}{2}, \frac{1}{2}$) disclination pattern in the assembled and photoaligned cell. FIG. 5(d) shows streamlines of electrokinetic flow caused by the ac electric field applied along the x axis and visualized by fluorescent 200 nm tracers. In FIG. 5, P and A represent the polarizer and analyzer, respectively.

Figure 6:
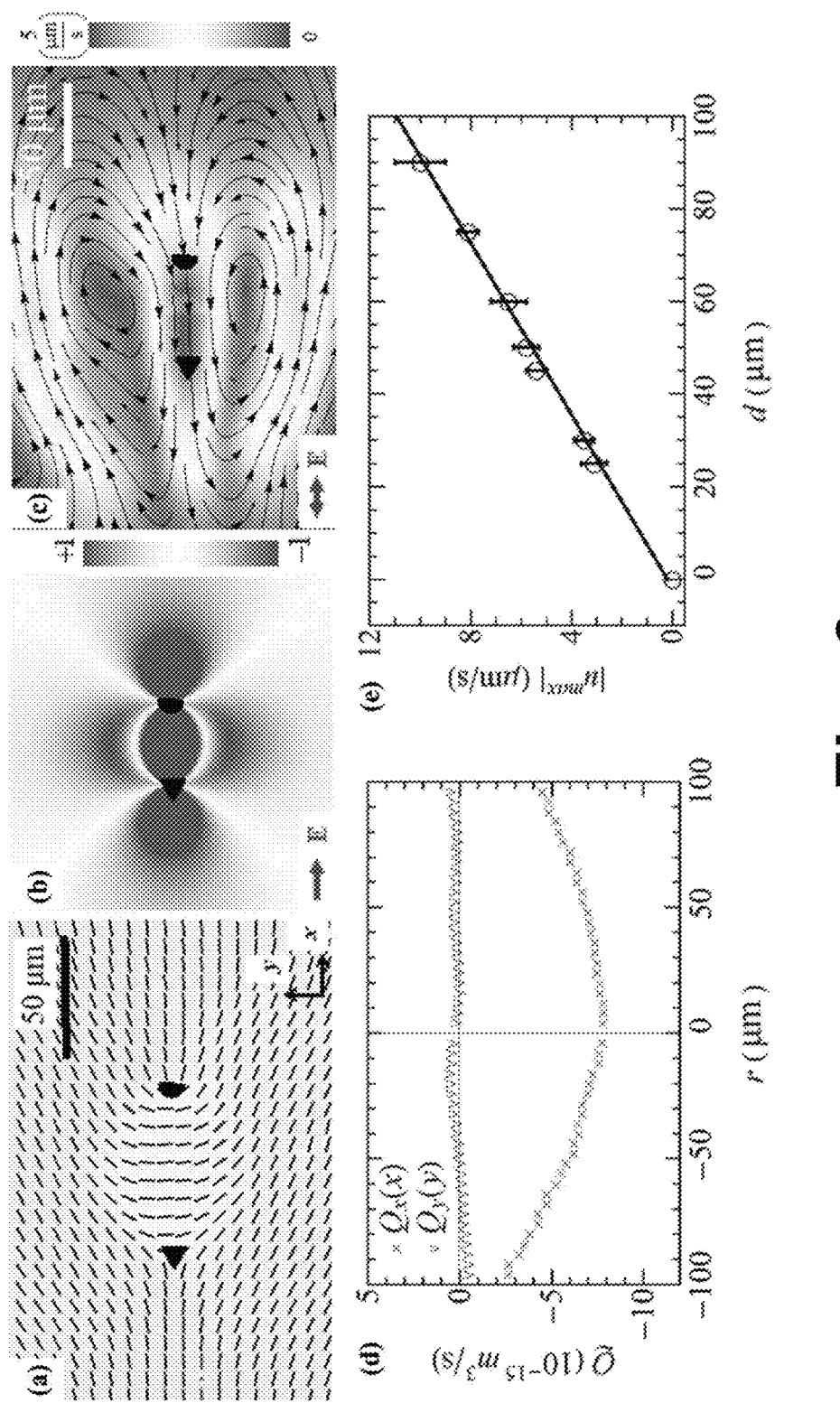

The director and flow patterns are further analyzed in FIG. 6, which illustrates nonlinear electrokinetic flows in LC electrolytes with pairs of topological defects. FIG. 6(a) shows PolScope texture of a nematic cell with disclination $-\frac{1}{2}$ (core marked by a triangle) and $\frac{1}{2}$ (core marked by a semicircle). FIG. 6(b) shows a map of spatially separated charges in a dc electric field. FIG. 6(c) shows velocity of LC flows caused by an ac field ($E_0$, 0). FIG. 6(d) shows the LC volume pumped per unit time along the x axis, $Q_x(x)$, and along the y axis, $Q_y(y)$. FIG. 6(e) shows the maximum electrokinetic flow velocity versus distance d between the disclinations.

Once the electric field is applied, the distorted director, FIG. 6a, creates a local charge density around the disclination pair that is shown in FIG. 6b. The map of positive and negative charges in FIG. 6b is derived from Equation (6) for $\sigma_\| > \sigma_\perp$ and $\epsilon_\perp = \epsilon_\|$. The resulting electrokinetic flow with two vortices, FIG. 6c, pumps the nematic from $\frac{1}{2}$ defect towards the $-\frac{1}{2}$ defect along the line joining the defects and in opposite direction above and below that line.

Pumping efficiency is quantified by the volumetric flow $$Q_x(x) = \frac{2}{3} h \int_{-y_0}^{y_0} u_x(x, y) dy$$

measured in the vertical xz cross-sections of the cell for each point along the x-axis in the range $|x| \leq x_0$, FIG. 6d, where h is the cell thickness. Here $x_0 = y_0 = 100$ μm; the horizontal component of velocity $u_x(x,y)$ is known from the experiment, FIG. 6c. The volumetric flow along the x-axis, $Q_x(x)$, is negative, reflecting the fore-aft asymmetry of the disclination pair, FIG. 6a. There is no net pumping along the y-axis, as $$Q_y(y) = \frac{2}{3} h \int_{-x_0}^{x_0} u_y(x, y) dx$$

is an antisymmetric function close to zero, as seen in FIG. 6d.

The maximum velocity measured in the center of the disclination pair grows linearly with the separation d between the defects, FIG. 6e. This result is understandable since the LCEK velocity u results from the balance of the driving force of density $f_x = \rho E_0 \propto \epsilon_0 \epsilon_\perp \Delta \sigma E_0^2/(d\sigma_\perp)$ and the viscous drag of density $f_{visc} \propto \eta u/d^2$; the estimate is $u \approx \beta \epsilon_0 \epsilon_\perp \Delta \sigma d E_0^2/(\eta \sigma_\perp) \propto d$, where $\beta$ is the numerical coefficient of the order of 1 that depends on the details of director configuration; the latter also defines the actual value of the (generally anisotropic) viscosity $\eta$.

Figure 7:
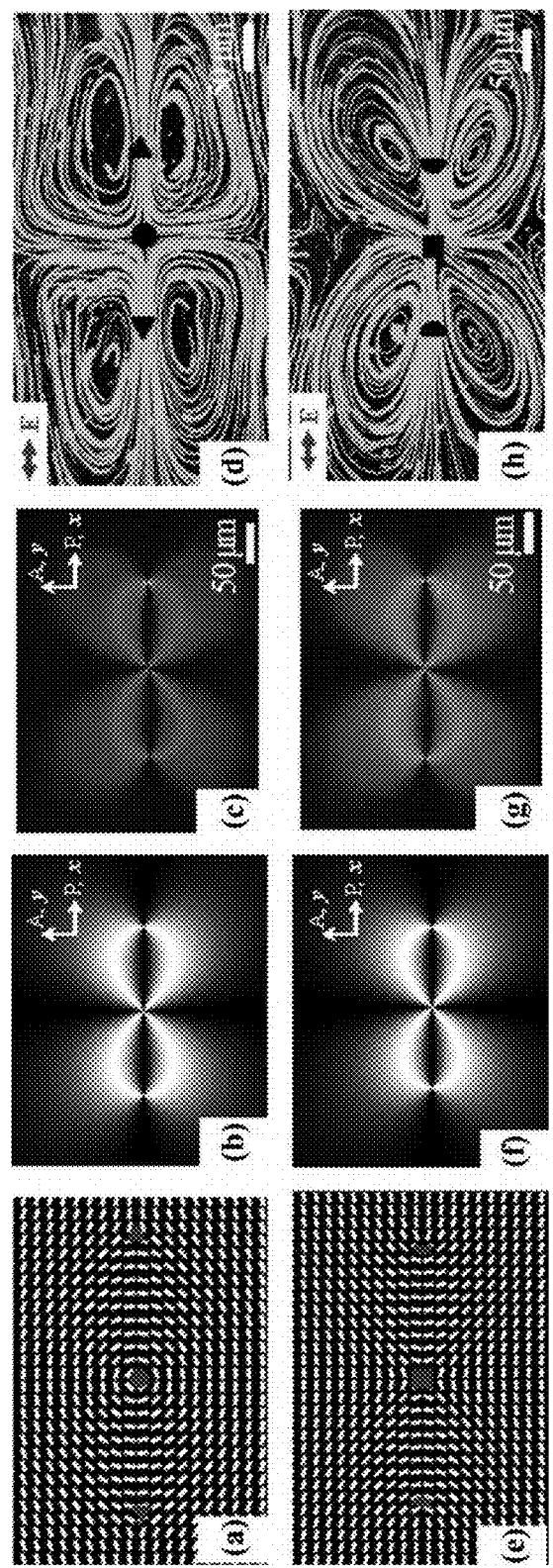

With reference now to FIG. 7, Triplets of defects are produced in a similar way with corresponding patterns of slits. FIGS. 7a and 7e illustrate slit patterns representing disclination triplets. FIG. 7a shows designed slit patterns for ($-\frac{1}{2}$, 1, $-\frac{1}{2}$) disclinations. FIG. 7e shows designed slit patterns for ($\frac{1}{2}$, $-1$, $\frac{1}{2}$) disclinations. FIGS. 7b and 7f show simulated polarizing microscopy texture of ($-\frac{1}{2}$, 1, $-\frac{1}{2}$) and ($\frac{1}{2}$, $-1$, $\frac{1}{2}$) disclinations, respectively. FIGS. 7c and 7g show polarizing microscopy texture of ($-\frac{1}{2}$, 1, $-\frac{1}{2}$) and ($\frac{1}{2}$, $-1$, $\frac{1}{2}$) sets of disclinations. Note a split character of the core of the integer-strength central defect. FIGS. 7d and 7h show streamlines of electrokinetic flow caused by ($-\frac{1}{2}$, 1, $-\frac{1}{2}$) and ($\frac{1}{2}$, $-1$, $\frac{1}{2}$) sets, caused by the AC electric field applied along the horizontal direction in the plane of the figure. P and A represent polarizer and analyzer respectively.

In FIG. 7, each triplet is comprised of two half-integer singular disclination at the periphery and a single integer-strength disclination in the center, as seen in FIGS. 7a and 7e. The integer-strength defects are unstable against splitting into pairs of half-integer disclinations, since the elastic energy of the director field around a disclination of strength m scales as $m^2$. As a result, the cores of the central defects are split into two closely separated individual cores with two extinction bands. Each of these individual cores represent a half-integer disclination, as seen in FIGS. 7c and 7g. The two cores are kept close to each other by the anchoring forces created by the photopatterned substrates. Because of the finite splitting of the central defect, each triplet configuration is in fact a set of four half-integer disclinations.

In terms of the produced electro-osmotic flows, the main feature of triplets is that they produce four vortices, as seen in FIGS. 7d and 7h. These patterns are analyzed in a greater detail in FIG. 8.

Figure 8:
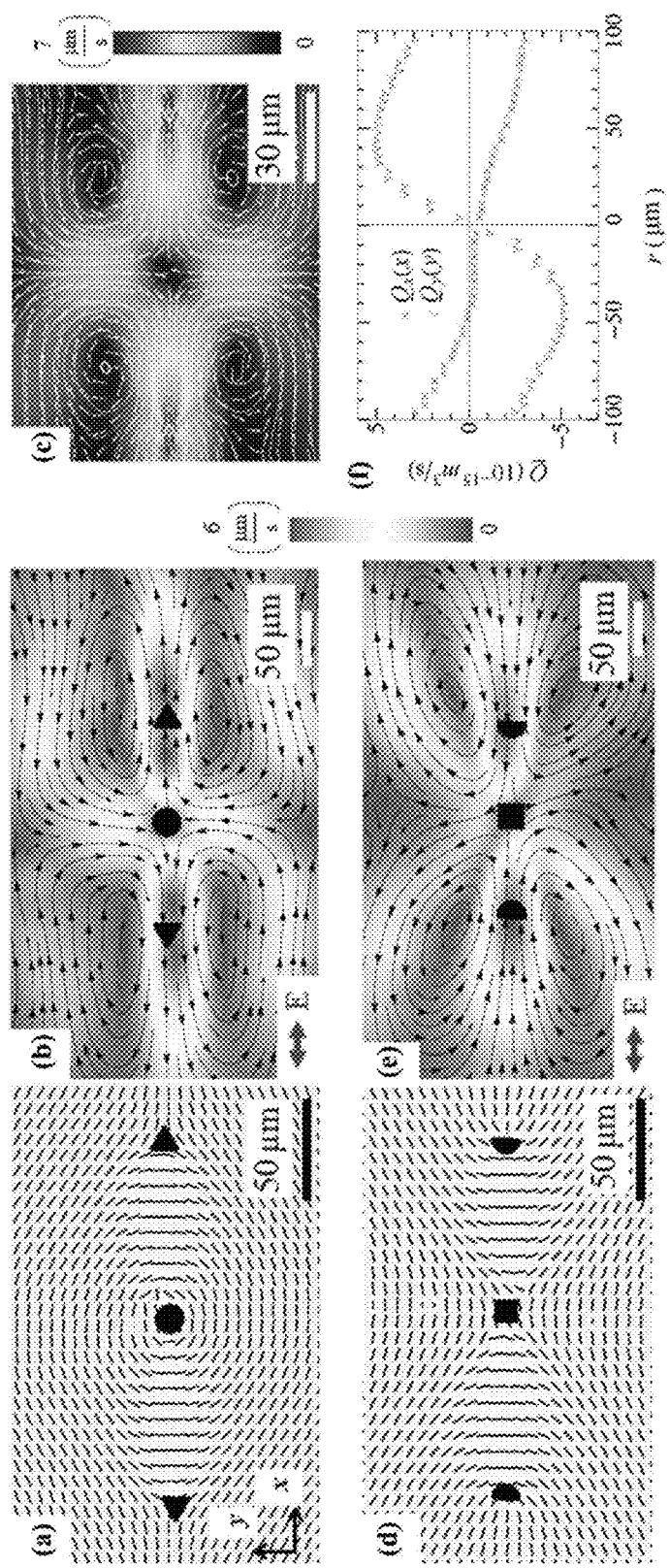

FIG. 8 shows nonlinear electrokinetic flows in LC electrolytes with triplets of topological defects. FIG. 8a shows PoiScope texture of a nematic cell with three disclinations ($-\frac{1}{2}$, 1, $-\frac{1}{2}$), ($-\frac{1}{2}$ core marked by a triangle, 1 core marked by a circle). FIG. 8b shows a corresponding velocity map of the nematic caused by the pattern in FIG. 8(a) caused by an AC electric field ($E_0$, 0). FIG. 8c shows numerically simulated electrokinetic flow velocity map. FIG. 8d shows PoiScope texture of disclinations ($\frac{1}{2}$, $-1$, $\frac{1}{2}$), ($\frac{1}{2}$ core marked by a semicircle, $-1$ core marked by a square). FIG. 8e shows a corresponding velocity map by the pattern in FIG. 8(d). FIG. 8f shows volume of nematic fluid pumped per unit time along the horizontal x axis, $Q_x(x)$, and along the y axis, $Q_y(y)$. The flow is of quadrupolar symmetry with four vortices and no pumping effect.

The ($-\frac{1}{2}$, 1, $-\frac{1}{2}$) triplet produces a flow of the "pusher" type, with the fluid moving from the central +1 defect (split into two closely located ½ disclinations) towards the two −½ disclinations at the periphery, as seen in FIG. 8b. A complementary triplet (½, −1, ½), produces the "puller" type of flows, with all flow directions being reversed, as seen in FIG. 8e. The reason is rooted in the nature of patterned LCEK, in which the separation of charges and flows depends on the director gradients.

To verify the disclosed mechanism of patterned LCEK, numerical simulations were performed of the flows for the three-defects set shown in FIG. 8a. The simulated velocity map (FIG. 8c), is in a good agreement with the experiment (FIG. 8b).

Surface patterning offers broad freedom in the design of flows. For example, a two-dimensional array of topological defects is designed in the form $n_x = \cos \alpha(x,y)$, $n_y = \sin \alpha(x,y)$ where:

$$\alpha(x, y) = \sum_{m,n} \left[ \tan^{-1} \frac{y+d_m}{x+d_n} - \frac{1}{2} \left( \tan^{-1} \frac{y+d_m}{x+d_n+d} + \tan^{-1} \frac{y+d_m}{x+d_n-d} \right) \right] + \sum_{p,q} \left[ \tan^{-1} \frac{y+d_p}{x+d_q} - \frac{1}{2} \left( \tan^{-1} \frac{y+d_p}{x+d_q+d} + \tan^{-1} \frac{y+d_p}{x+d_q-d} \right) \right] \tag{10}$$

where $d_m = \sqrt{3}md$, $m=0, \pm1, \pm2, \ldots$, $d_n = 3nd$, $n=0, \pm1, \pm2, \ldots$, $$d_p = \frac{\sqrt{3}}{2}(2p+1)d,$$

$p=0, \pm1, \pm2, \ldots$, $$d_q = \frac{3}{2}(2q+1)d,$$

$q=0, \pm1, \pm2, \ldots$, and d is the distance between the defects of strength 1 and −½. Typical values of m, n, p, and q in the photomasks were 4-5.

Figure 9:
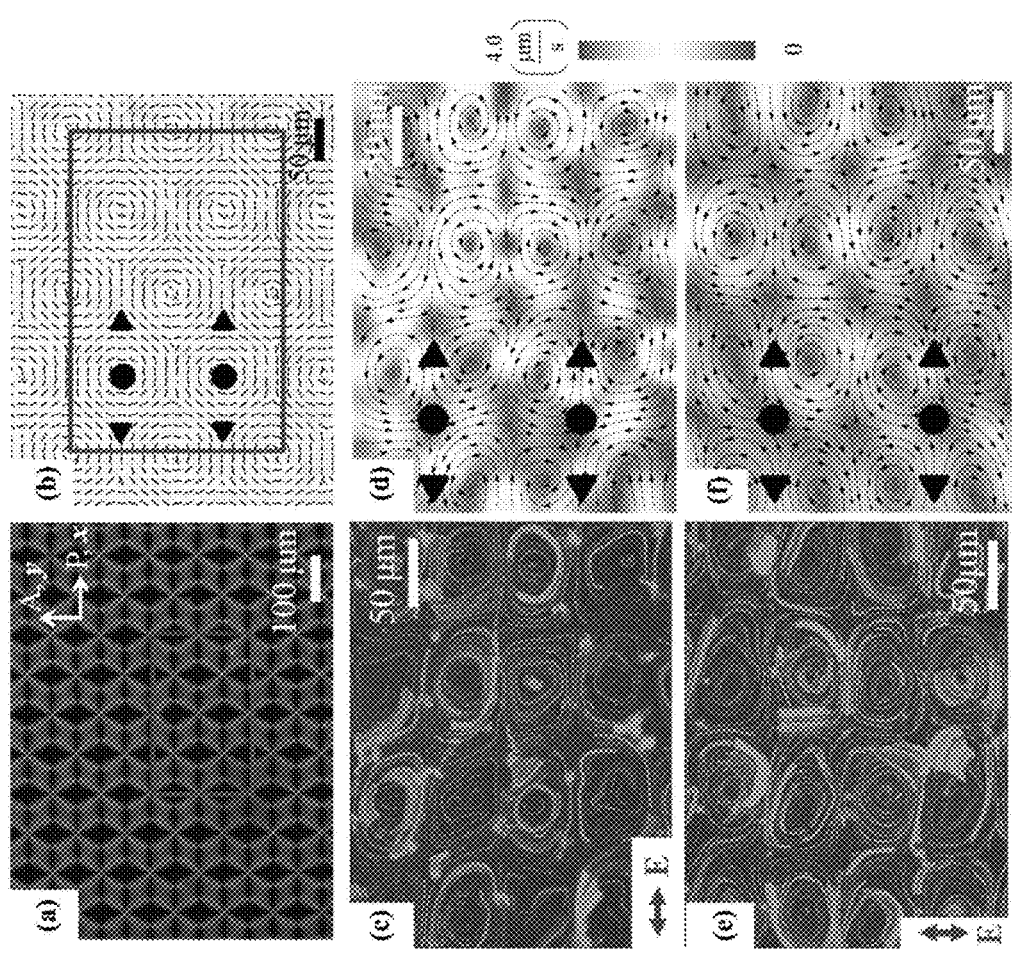

With reference to FIG. 9, the two-dimensional array of vortices of LCEK flows with clockwise and anticlockwise rotation can be achieved by this two-dimensional lattice. FIG. 9 shows nonlinear electrokinetic flows in LC electrolytes with patterns of two-dimensional lattice of topological defects. FIG. 9a shows polarizing microscopy texture of a periodic array of disclinations. FIG. 9b shows PolScope texture of the area indicated in FIG. 9a. FIG. 9c shows streamlines of electrokinetic flow caused by the AC electric field along the x-axis and visualized by fluorescent 200 nm tracers. FIG. 9d shows a corresponding velocity field in the same region. FIG. 9e shows streamlines of electrokinetic flow caused by the AC electric field acting along the y-axis. FIG. 9f shows a corresponding velocity field.

In the example of FIG. 9, the polarity of each and every vortex can be reversed by a simple reorientation of the electric field, from $E=(E_0, 0)$ for FIGS. 9c and 9d, to $E=(0, E_0)$ for FIGS. 9e and 9f. Another degree of freedom is provided by the reversible character of photoalignment in LCs that can be repeatedly written and rewritten. By using photoinduced trans-cis isomerization that triggers homeotropic-planar realignment at the bounding substrates, one can steer the clusters of LCEK-active colloids with the pear-like shapes. The asymmetric shape creates asymmetric distortions around the particle and enables the propulsion; the role of photo-induced re-alignment is to steer the overall direction of motion. It is contemplated to expand this approach to the substrate-controlled LCEK, by creating and then realigning the director distortions at the substrate that trigger the LCEK flows and transport.

In the following, transport of solid, fluid, and gaseous "cargo" in patterned LCEK flows is considered.

Figure 10:
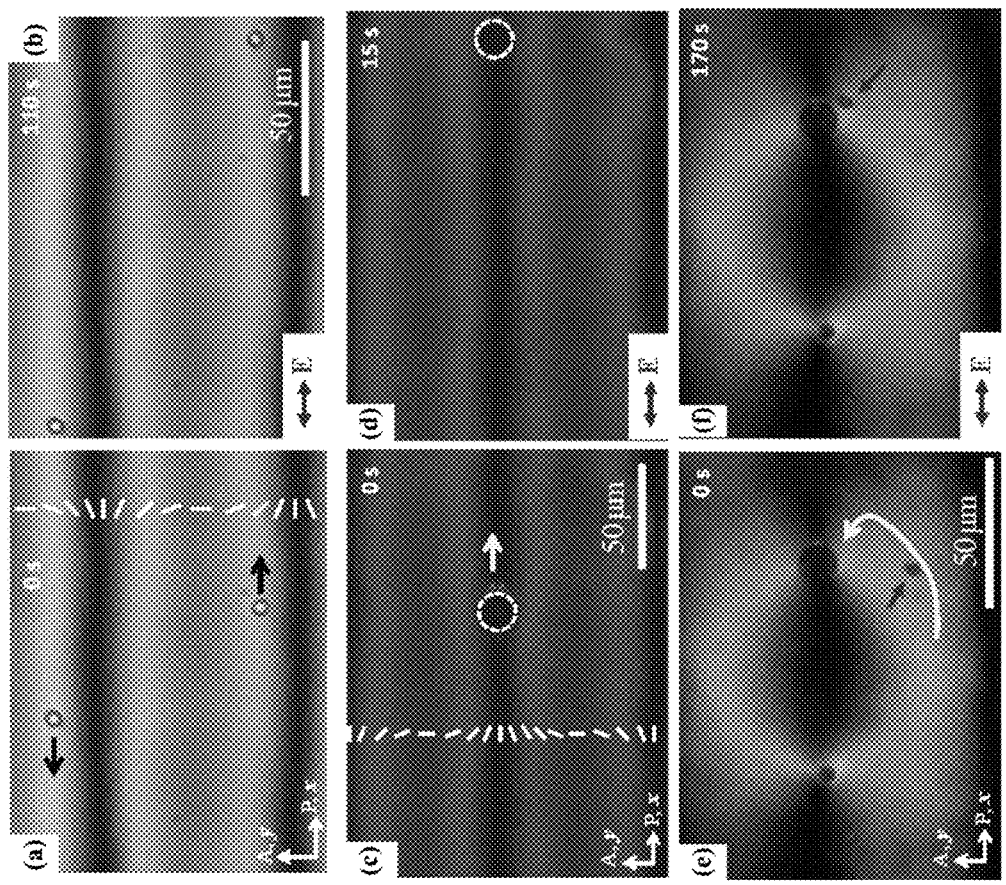
FIG. 10 illustrates transport by electrokinetic flow.

With reference to FIG. 10, electrokinetic flows can be used to transport particles. FIGS. 10a and 10b illustrate transport of polystyrene spheres dispersed in the LC. FIGS. 10c and d illustrate transport of air bubbles. FIGS. 10e and 10f illustrate transport of other fluids, e.g. water. More particularly, FIGS. 10a and 10 show linear transport of two polystyrene particles of diameter 5 μm in the LC with the periodic pattern shown in FIG. 4a. FIGS. 10c and 10d show linear transport of an air bubble (profiled by a dashed circle) in the nematic chamber with periodic director pattern. FIGS. 10e and 10f show LC flows carrying a water droplet (marked by a small arrow) doped with the dye Brilliant Yellow in the nematic chamber with (−½, ½) disclination pattern shown in FIG. 6a. The trajectory is shown by a curved arrow. The droplet is transported towards the core of the ½ disclination on the right hand side and coalesces with another water droplet that is already trapped there.

The LCEK directed by surface patterning does not impose any limitations on the properties of the "cargo", such as separation of surface charges, polarizability or ability to distort the LC. The latter feature is especially important as compared to the effects of colloidal transport in an otherwise uniform LC cell caused by asymmetric director distortions at the surface of the particle. In particular, the polystyrene sphere transport (FIGS. 10a and 10b) and water droplet transport (FIGS. 10e and 10f) show tangential anchoring of the director at their surfaces. Because the director distortions in this case are of quadrupolar symmetry, these particles with tangential anchoring do not move in a uniformly aligned LC cell. In the patterned LCEK, however, these particles do move as the electric field energy is rectified at the gradients created in the LC medium by the substrates and there is no need for the transported particle to exhibit any particular surface anchoring properties.

The trajectory of the cargo transport by LCEK is determined by the pattern of molecular orientation. For example, in the conveyor's configurations, the solid sphere (FIGS. 10a and 10b) and air bubble (FIGS. 10c and 10d) move along straight segments. A very different scenario is shown in FIGS. 10e and 10f—there, the water droplet moves within a vortex along the velocity streams illustrated in FIG. 6c and is trapped at the core of the +½ disclination, joining another water droplets already trapped there; the effect can be used to create micro-scale chemical reactors.

Micro-mixing by patterned LC-enabled electrokinetic flows is next considered. Surface-imprinted director patterns can be used to facilitate mixing. The circular director distortion is designed as:

$$(n_x, n_y) = \left( \cos\left(\tan^{-1}\frac{y}{x}\right)\cos\sqrt{x^2+y^2} - \sin\left(\tan^{-1}\frac{y}{x}\right) \times \left|\sin\sqrt{x^2+y^2}\right|, \right. \\ \left. \sin\left(\tan^{-1}\frac{y}{x}\right)\cos\sqrt{x^2+y^2} + \cos\left(\tan^{-1}\frac{y}{x}\right)\left|\sin\sqrt{x^2+y^2}\right| \right) \tag{11}$$

Figure 11:
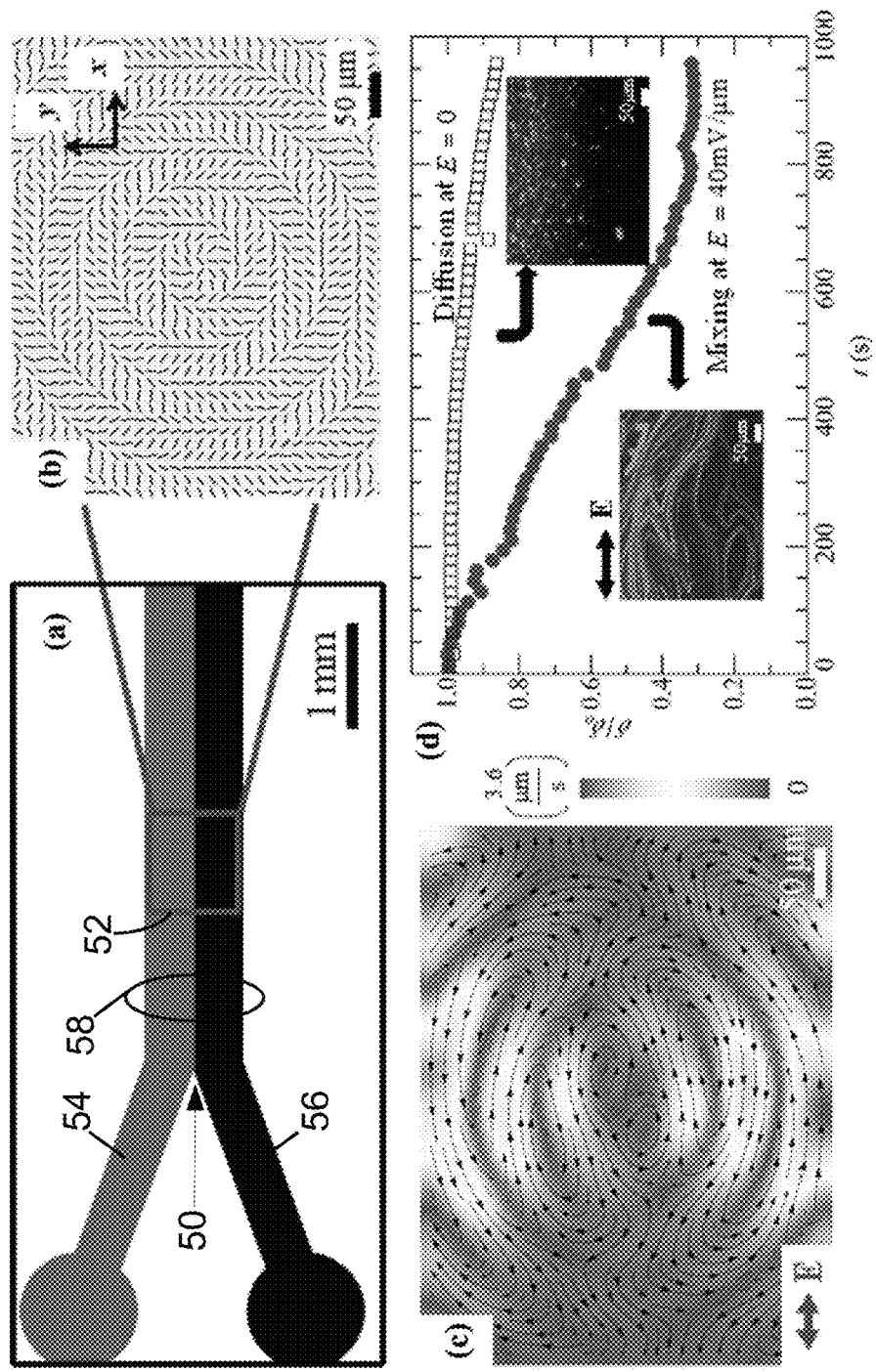
FIG. 11 illustrates micromixing in a Y-junction with photopatterned director distortions.

With reference to FIG. 11, an illustrative example of micromixing in a Y-junction with photopatterned director distortions is shown. FIG. 11a shows the Y-junction 50 with a photo-imprinted mixing pad 52 (the indicated square) that combines the LC with fluorescent particles (upper path 54) and pure LC (lower path 56). FIG. 11b shows PolScope texture of the mixing pad 52. This texture is in accord with the circular director distortion of Equation (11). FIG. 11c shows velocity maps within the mixing pad 52. FIG. 11d shows a comparison of mixing efficiencies of passive diffusion (E=0) and LCEK (E=40 mV/μm). In FIG. 11d, the insets show the fluorescence microscopy textures of the mixing pad with the exposure time interval 550 s after the start of mixing.

In the experiments of FIG. 11, the cell 52 with the distortions as per Equation (11) was placed in a microfluidic channel 58, right after the Y-junction 50 at which two fluids are combined from the respective upper and lower paths 54, 56 into one channel 58. The top inlet 54 was injected with a LC containing 200 nm fluorescent tracers and bottom inlet 56 was injected with a pure LC. If there is no electric filed, mixing is achieved only by slow diffusion (low Reynolds number regime). To characterize the mixing efficiency, FIG. 11d plots the normalized standard deviation $\delta/\delta_0$ in fluorescent intensity of the patterns, as a function of time. Here $\delta_0=1/2$. In the completely unmixed state, $\delta/\delta_0=1$ and then decreases towards 0 as the two components mix. FIG. 11d presents a comparison of the mixing efficiency assisted by LCEK (circles) and mixing efficiency of pure diffusion at zero electric field (squares). As clearly seen in FIG. 11d, mixing assisted by LCEK progresses much faster than mixing driven by diffusion only. Advantageously, the disclosed LC mixers do not require any mechanical parts, pressure gradients, nor complicated system of electrodes and ridges that can obstruct the flow.

An intriguing question about the experimental setup is how far the director distortions produced by photoalignment at the bounding substrates can propagate into the bulk of the LC. Generally, in absence of any other external aligning factors, the surface-induced alignment is replicated into the LC bulk over macroscopic distances. This is certainly true for the cells used in the here-described experiments, of thickness 50 μm. In these (and thinner) cells, the disclination lines are joining the top and bottom plates 12, 14 (see FIG. 1) along the vertical z-axis, regardless of whether the electric field is applied or not. The situation might change when the thickness of the cell h becomes substantially larger that the characteristic spatial scales l and d of the in-plane director distortions. In this case, the LC might relax through bulk director configurations that are different from the surface patterns. Consider a disclination pair as an example. The elastic energy of a disclination is proportional to its length and to the elastic modulus K of the LC. If h is smaller than the in-plane separation d between the two disclinations, the defects are vertical with the total energy ~2 Kh. If h>d, however, the disclinations would tend to reduce their total energy to ~2 Kd by reconnecting the points at the same substrate. Therefore, the surface-induced pattern of director distortions is expected to persist in the bulk as long as h≤l, d. Furthermore, because of the finite anchoring strength produced by photoalignment, the in-plane director deviates from the imposed surface alignment when the in-plane director gradients become larger than some critical value (equal about 0.2 $\mu m^{-1}$ in experiments reported herein).

As disclosed herein, the spatially varying director field of an LC electrolyte achieved through photo-imprinted surface alignment allows for the creation of electrokinetic flows of practically any complexity and vorticity. The flows are persistent, as their velocities are proportional to the square of the applied field, so that the driving field can be of an AC type. The transport of LC and particles dispersed in it is easily controlled by the predesigned director gradients; no mechanical parts and no external pressure gradients are needed. The flow polarity can be changed either by changing the director patterns or the electric field direction. Since the charges are separated in the bulk of electrolytic LC medium rather than at the solid-liquid interfaces, the disclosed approach eliminates the need for polarizable/charged interfaces. For example, experiments reported herein demonstrate that LCEK created by surface patterns can carry inclusions such as solid colloids, droplets of water and air bubbles even if these inclusions have no electrophoretic activity (zero charge or zero polarizability) on their own. The cross-sections of the patterned LC microfluidic chambers are not obstructed by any barriers (such as ridges, electrode posts or colloidal particles, needed in other electrokinetic devices), thus combining efficiency of flows with simplicity of design.

The disclosed approach is suitable for lab-on-the-chip and microfluidic devices. From the fundamental point of view, the described patterned LC electrolyte represents a new type of active matter in which the energy input that drives the system out of equilibrium occurs locally through orientation distortions of the medium rather than at the particles dispersed in it. This is a significant practical difference as compared to active materials with artificial or biological swimmers embedded in an otherwise inert surrounding medium such as water. The patterned LC electrolytes add a new dimension to active systems, as both the medium and the dispersed particles can be used for energy input and departure from equilibrium.

It will be appreciated that various of the above-disclosed and other features and functions, or alternatives thereof, may be desirably combined into many other different systems or applications. It will be further appreciated that various presently unforeseen or unanticipated alternatives, modifications, variations or improvements therein may be subsequently made by those skilled in the art which are also intended to be encompassed by the following claims.

The invention claimed is:

1. A transport device comprising:
   a fluid cell comprising parallel substrates;
   an anisotropic electrolyte disposed in the fluid cell; and
   electrodes configured to apply an AC electric field to the anisotropic electrolyte disposed in the fluid cell;
   wherein a substrate of the fluid cell includes a pattern that induces a director distortion pattern in the anisotropic electrolyte disposed in the fluid cell, the director distortion pattern having a gradient configured by the director distortion pattern being one-dimensionally periodic or having a two-dimensional array of topological defects to induce electrokinetic flow of the anisotropic electrolyte in the fluid cell in response to the AC electric field applied by the electrodes.

2. The transport device of claim 1 further comprising:
   Particles, gas bubbles, or droplets dispersed in the anisotropic electrolyte,
   wherein the electrokinetic flow of the anisotropic electrolyte induced in the fluid cell in response to the AC electric field applied by the electrodes is effective to transport the particles, gas bubbles, or droplets in the fluid cell.

3. The transport device of claim 1 wherein the fluid cell includes:

plural fluid inlets combined at a junction into a combined fluid channel;

wherein the gradient of the induced director distortion pattern is configured to induce the electrokinetic flow as an electrokinetic mixing flow of the anisotropic electrolyte in the combined fluid channel in response to the AC electric field applied by the electrodes whereby different cargo flowed into the fluid cell via the plural fluid inlets are mixed by operation of the electrokinetic mixing flow of the anisotropic electrolyte.

4. The transport device of claim 1 wherein the director distortion pattern includes at least one disclination and the gradient of the director distortion pattern is configured to induce electrokinetic flow of the anisotropic electrolyte in the fluid cell toward a core of the at least one disclination in response to the AC electric field applied by the electrodes.

5. The transport device of claim 4 further comprising:
cargo disposed in the anisotropic electrolyte;
wherein the induced electrokinetic flow of the anisotropic electrolyte in the fluid cell toward the core of the at least one disclination operates to trap the cargo at the core of the at least one disclination.

6. The transport device of claim 5 wherein the cargo is chemically reactive whereby the transport device comprises a micro-scale chemical reactor.

7. The transport device of claim 1 wherein the director distortion pattern includes at least one disclination and the gradient of the director distortion pattern is configured to induce electrokinetic flow of the anisotropic electrolyte in the fluid cell away from a core of the at least one disclination in response to the AC electric field applied by the electrodes.

8. The transport device of claim 1 wherein the gradient of the director distortion pattern is configured to induce linear electrokinetic flow of the anisotropic electrolyte in the fluid cell in response to the A.C. electric field applied by the electrodes.

9. The transport device of claim 1 wherein the electrodes are configured to apply the AC electric field with zero average to the anisotropic electrolyte disposed in the fluid cell and the gradient of the director distortion pattern induces electrokinetic flow of the anisotropic electrolyte in the fluid cell in response to the AC electric field with zero average applied by the electrodes.

10. The transport device of claim 1 further comprising:
a photosensitive material disposed on the substrate, wherein the pattern of the substrate that induces the director distortion pattern is a photoinduced pattern formed in the photosensitive material disposed on the substrate.

11. The transport device of claim 1 wherein the electrokinetic flow of the anisotropic electrolyte in the fluid cell induced by the gradient in response to the AC electric field applied by the electrodes is independent of any colloidal particles carried by the electrokinetic flow of the anisotropic electrolyte in the fluid cell.

12. The transport device of claim 1 wherein the director distortion pattern has the gradient configured by the director distortion pattern being one-dimensionally periodic to induce electrokinetic flow of the anisotropic electrolyte in the fluid cell in response to the AC electric field applied by the electrodes.

13. The transport device of claim 1 wherein the director distortion pattern has the gradient configured by the director distortion pattern having a two-dimensional array of topological defects to induce electrokinetic flow of the anisotropic electrolyte in the fluid cell in response to the AC electric field applied by the electrodes.

14. The transport device of claim 13 wherein the topological defects of the two-dimensional array of topological defects are pairs or triplets of disclinations.

15. A transport method comprising:
inducing a director distortion pattern in an anisotropic electrolyte disposed in a fluid cell wherein the induced director distortion pattern has a gradient configured to induce electrokinetic flow of the anisotropic electrolyte;
applying an AC electric field to the anisotropic electrolyte disposed in the fluid cell whereby electrokinetic flow of the anisotropic electrolyte is induced; and
flowing different cargo into the fluid cell via different inlets;
wherein the gradient of the induced director distortion pattern is configured to induce an electrokinetic flow of the anisotropic electrolyte whereby the different cargo flowed into the fluid cell via the different inlets are mixed by operation of the electrokinetic flow of the anisotropic electrolyte.

16. The transport method of claim 15 wherein the inducing comprises:
forming a pattern on a substrate of the fluid cell, the pattern inducing the director distortion pattern.

17. The transport method of claim 15 further comprising:
disposing a cargo in the anisotropic electrolyte;
wherein the induced electrokinetic flow of the anisotropic electrolyte transports the cargo in the fluid cell.

18. The transport method of claim 15 wherein the gradient of the induced director distortion pattern is configured to induce the electrokinetic flow as a circular electrokinetic flow of the anisotropic electrolyte whereby the different cargo flowed into the fluid cell via the different inlets are mixed by operation of the circular electrokinetic flow of the anisotropic electrolyte.

19. A transport method comprising:
inducing a director distortion pattern in an anisotropic electrolyte disposed in a fluid cell wherein the induced director distortion pattern has a gradient configured to induce electrokinetic flow of the anisotropic electrolyte and wherein the inducing comprises performing patterned photoalignment of a photosensitive layer disposed on the substrate using a plasmonic mask with nanoslits; and
applying an AC electric field to the anisotropic electrolyte disposed in the fluid cell whereby electrokinetic flow of the anisotropic electrolyte is induced.

20. The transport method of claim 19 wherein the director distortion pattern includes a disclination and the applying comprises:
applying the AC electric field to the anisotropic electrolyte disposed in the fluid cell whereby electrokinetic flow of the anisotropic electrolyte to a core of the disclination is induced.

21. The transport method of claim 20 further comprising:
disposing chemical reactants in the anisotropic electrolyte;
wherein the electrokinetic flow of the anisotropic electrolyte to the core of the disclination operates as a micro-scale chemical reactor.

* * * * *